(12) United States Patent
Saghbini et al.

(10) Patent No.: US 8,174,392 B1
(45) Date of Patent: May 8, 2012

(54) RFID MEDICAL ITEM HANGING STORAGE SYSTEM

(75) Inventors: Jean-Claude J. Saghbini, Cambridge, MA (US); James Billington, North Attleboro, MA (US); Daniel W. Johnson, North Chelmsford, MA (US)

(73) Assignee: WaveMark, Inc., Littleton, MA (US)

( * ) Notice: Subject to any disclaimer, the term of this patent is extended or adjusted under 35 U.S.C. 154(b) by 430 days.

(21) Appl. No.: 12/258,847

(22) Filed: Oct. 27, 2008

(51) Int. Cl.
| | |
|---|---|
| G08B 13/14 | (2006.01) |
| G05B 19/00 | (2006.01) |
| G06F 19/00 | (2011.01) |
| G06F 7/00 | (2006.01) |
| G06Q 10/00 | (2012.01) |

(52) U.S. Cl. .......... 340/572.8; 340/572.7; 340/5.92; 235/385; 700/214; 705/28

(58) Field of Classification Search ........ 340/572.7, 340/572.8, 286.07, 539.12, 5.61, 5.73, 5.9, 340/5.92, 10.1–10.6; 235/375–385; 700/213–230; 40/299.01

See application file for complete search history.

(56) References Cited

U.S. PATENT DOCUMENTS

| | | | | |
|---|---|---|---|---|
| 4,132,309 | A  * | 1/1979 | Shaylor | 206/278 |
| 6,811,064 | B2 * | 11/2004 | Salem | 223/94 |
| 7,015,815 | B1 * | 3/2006 | Feibelman | 340/572.8 |
| 7,286,900 | B1 * | 10/2007 | Frederick et al. | 700/242 |
| 7,648,065 | B2 * | 1/2010 | Marino | 235/383 |
| 2002/0196126 | A1 * | 12/2002 | Eisenberg et al. | 340/10.2 |
| 2005/0099303 | A1 * | 5/2005 | Zuckerman | 340/572.8 |
| 2006/0265246 | A1 * | 11/2006 | Hoag | 705/2 |

* cited by examiner

*Primary Examiner* — Benjamin C Lee
*Assistant Examiner* — Omeed Alizada
(74) *Attorney, Agent, or Firm* — Houston Eliseeva LLP

(57) ABSTRACT

A medical item hanging storage system for medical items having stand-off readable tags, such as RFID tags, comprises storage devices comprising fixtures for holding hanging medical items, and readers for reading tags associated with each of the medical items, and tags that attached to the hanging medical items to be read by the readers. Tagging devices are used for attaching the RFID tags. The tagging devices each comprise a substrate, possibly including a hook, an adhesive portion for attaching the substrate to the medical item, and at least one spreader for separating RFID tags of adjacent medical items and/or other tags to facilitate reading of the tags.

9 Claims, 3 Drawing Sheets

RFID MEDICAL ITEM HANGING STORAGE SYSTEM

BACKGROUND OF THE INVENTION

Radio Frequency Identification (RFID) systems have been proposed for the tracking of medical item supplies in hospitals and the entire medical item supply chain. Such systems typically involve one or more readers and many RFID tags, each of which is associated with, such as attached to, items being monitored or tracked. In the case of pharmaceuticals, single-use medical devices, and implantable medical devices, RFID tags are typically affixed to or made part of the pharmaceutical containers, e.g., medicine bottle, or medical device container, e.g., disposable packaging for the stent or orthopedic implant. An advantage of RFID tags is that they are stand-off readable, i.e., readable at a distance without a requirement for contact or a direct line of sight path between the reader and the tag.

RFID tags take the form of integrated circuits, with associated antennas, that encode unique serial numbers. The reader can be in a fixed location or mobile with an operator, and items with RFID tags are detected when they enter or leave the electromagnetic field of the reader. For example, RFID readers are often placed at multiple, distributed locations associated within a supply chain in order to monitor the items as they pass through manufacturing, transportation, distribution, storage, to consumption. Each reader captures the RFID tag serial numbers of each item as it enters the reader's interrogation field, and data collected from all readers facilitate item tracking over time, through and within the chain.

Typically, the RFID tags are associated with medical items by affixing them to the medical item packaging. In this way, by tracking the RFID tag, the medical item is tracked in and between the hospital or distribution center or manufacturer.

Such RFID tagged medical items can be stored in storage devices, such as cabinets, that automatically scan the RFID-tagged items contained in the storage devices. In some examples, medical cabinets are provided with RFID reader antennas that are periodically moved or scanned over the length of the cabinets to enable the RFID readers to scan for RFID tags on medical item packages in the storage cabinets. This antenna scanning facilitates detection of the tags regardless of orientation within the cabinets or proximity to other RFID tags. In other examples, stationary antennas are used, when scanning is not required antenna arrays are used.

SUMMARY OF THE INVENTION

While some medical items are packaged in boxes for storage, typically on shelves, other medical items are packaged for hanging storage. This is especially common in the case of medical fluids, which are often stored in bags and other products that should not be laid flat or are more space-efficiently stored in a hanging arrangement.

In general, according to one aspect, the invention features a medical item hanging storage system for medical items having stand-off readable tags, such as RFID tags. The system comprises storage devices comprising fixtures for holding hanging medical items, and readers for reading tags associated with each of the medical items, and tags that attached to the hanging medical items to be read by the readers.

In the preferred embodiment, the antennas of the readers are integrated into members located above the fixtures in the storage devices, such as into shelves in the storage devices.

Further in the preferred embodiment, tag substrates are used, the tags being affixed to the substrates and the substrates being affixed to the hanging medical items. In one example, the tag substrates engage the fixtures, using hooks, for example, with the hanging medical items being supported on the fixtures via the tag substrates.

Spreaders are often necessary to ensure that tags are separated by sufficient space. The spreaders separate RFID tags of adjacent medical items from each other to facilitate reading of the tags by the readers. In some cases, the spreaders are attached to the tag substrates. In other cases, the spreaders are formed by folding the tag substrates.

In general according to another aspect, the invention features a method for storing and tracking medical items. The method comprises providing fixtures for holding medical items in a hanging arrangement, reading stand-off readable tags associated with each of the medical items, and providing spreaders for separating stand-off readable tags of adjacent medical items and/or other tags to facilitate reading of the tags.

In general according to still another aspect, the invention features a medical item tagging device comprising a substrate including a hook portion for hanging on a fixture, an adhesive portion for attaching the substrate to a medical item, and an RFID tag attached to the substrate.

In general according to still another aspect, the invention features a medical item tagging device comprising a substrate, an adhesive portion for attaching the substrate to a medical item, an RFID tag attached to the substrate, and at least one spreader for separating stand-off readable tags of adjacent medical items and/or other tags to facilitate reading of the tags.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
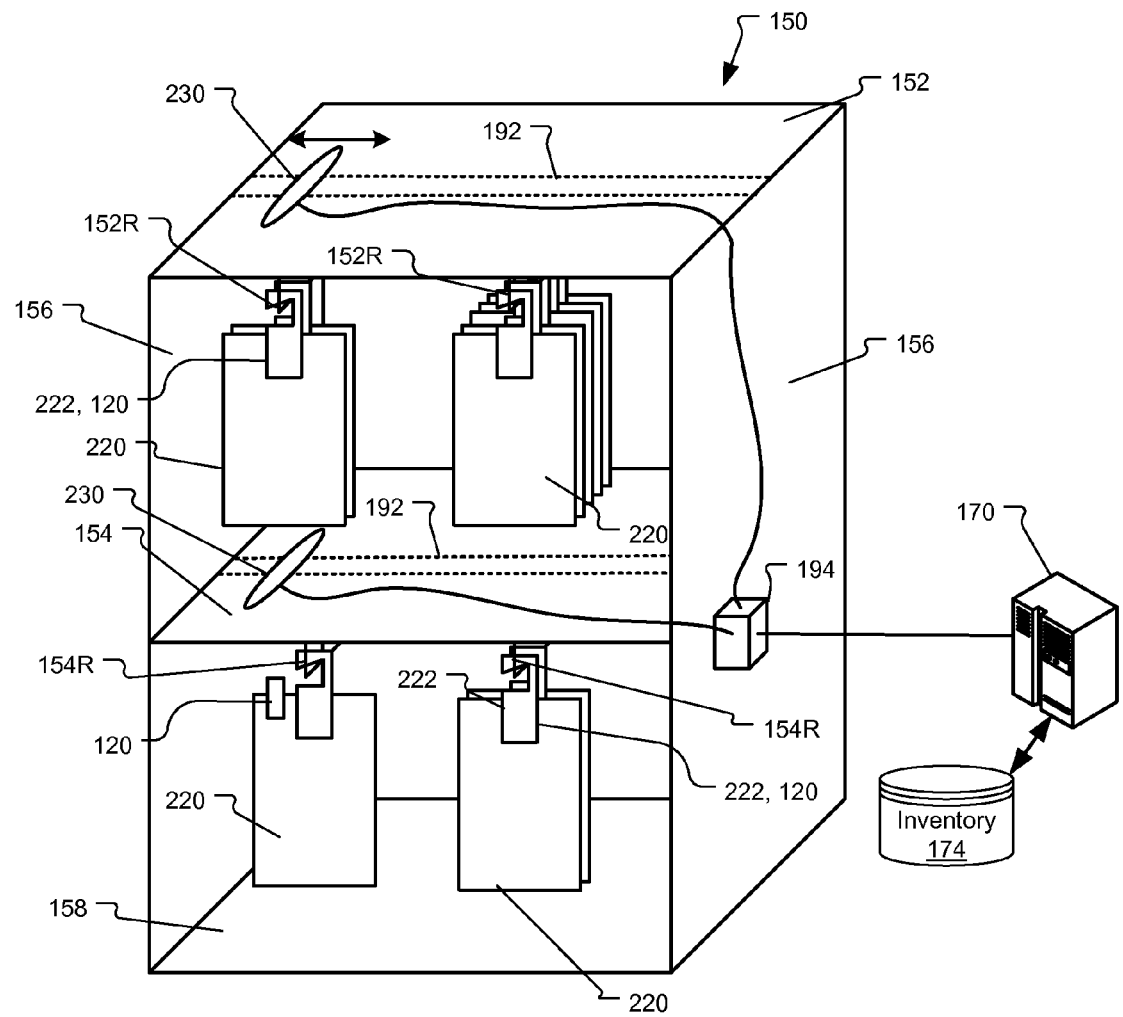
FIG. 1 is a schematic perspective view of an RFID cabinet storage device for holding hanging medical items according to the present invention.

FIG. 1 shows an RFID cabinet storage device 150, which has been constructed according to the principals of the present invention.

The cabinet 150 contains hanging medical items 220. Medical devices, a subclass of medical items, include a broad range of devices including classes of devices such as implanted devices (e.g., cardiac stents and joint replacements), disposables (e.g., catheters and hypodermic syringes), and equipment (e.g., imaging and monitoring devices), for example. Similarly, pharmaceuticals, another subclass of medical items, are manufactured by the pharmaceutical manufacturers, e.g., drug companies. Specific examples of medical item that are stored in a hanging arrangement include blood products, e.g., saline solution, and chemo-therapy drugs.

In the illustrated embodiment, the cabinet has a top wall 152, left and right side walls 156, and a bottom wall 158. A shelf 154 separates the cabinet's interior space into upper and lower storage regions.

The top wall 152 and the shelf 154 each include RFID scanning systems, which interrogate the RFID tags of the items 220. Each RFID scanning system includes one or more cabinet antennas 230. In the illustrated example, the antennas 230 of the RFID scanning systems are scanned along the length of the cabinet 150 on an antenna conveyor 192. An RFID controller 194 for the cabinet 150 uses the information from the antennas 230 to read the RFID tags of the items 220 contained in the cabinet 150. The information is transmitted via a network interface to an inventory management system 170 that then stores inventory information in an inventory database 174, which is indexed by the read tag information.

Hanging from the bottom of the top wall 152 and the shelf 154 are fixtures, such as hanging rods, 152R, 154R. Typically, each of the top wall 152 and shelf has two or more hanging fixtures 152R, 154R. Each of the medical items 220 is held in the cabinet in a hanging arrangement with respect to the fixtures 152R, 154R. In the illustrated example, each of the medical items has a hook 222 that engages the fixtures 152R, 154R.

The RFID tags are integrated into tagging devices 120 that are associated with the items. In some examples, the tagging devices are separate tags that are attached, such as adhered, onto the medical items packaging. In other examples, the tagging devices are integrated into the hooks 222.

Figure 2A:
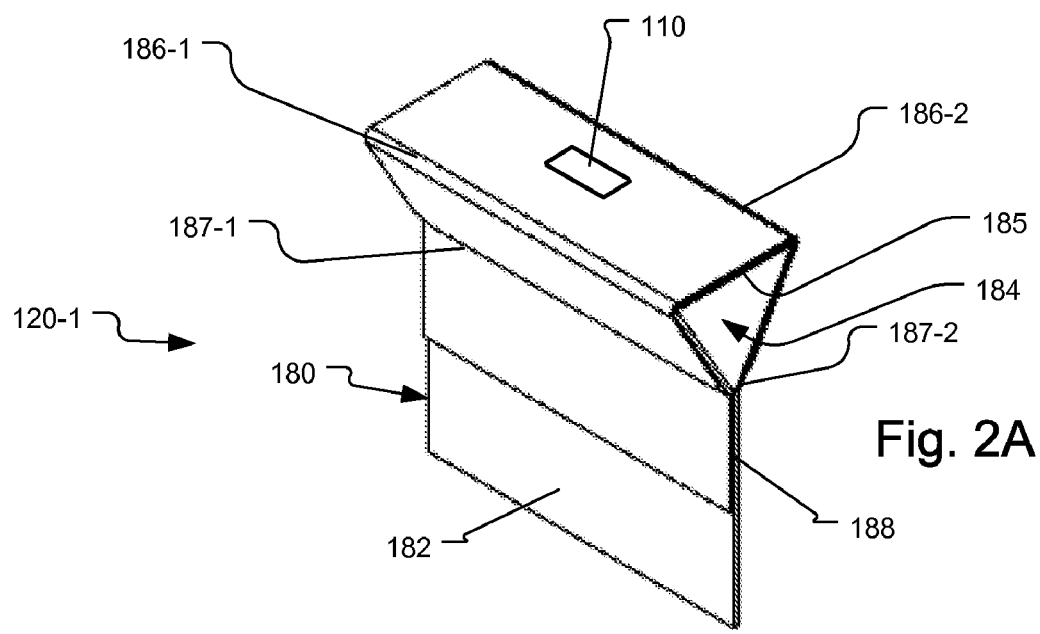
FIGS. 2A and 2B are perspective views of two RFID tags and substrates according to a first and second embodiments of the present invention.

FIG. 2A shows a first embodiment of the RFID tagging device, 120-1. The tagging device 120-1 comprises a RFID tag substrate 180. In this embodiment, the tag substrate 180 is formed from a folded piece of plastic or thin cardboard. Specifically, a series of folds 186-1, 186-2, 187-1, 187-2 are provided. Two outside folds 187-1, 187-2 are provided on either side of two inside folds 186-1, 186-2. Thus, by gluing the substrate together at region 188, a triangular cross-section-volumetric region 184 is defined near the center of the substrate 180. In a preferred embodiment, the RFID tag or label 110 is adhered to lateral section 185 between the two inside folds 186-1, 186-2 and over the triangular volumetric region 184 of the folded substrate 180. The lateral section 185 functions as a spreader and in combination with the triangular volumetric region 184 ensures that the RFID tag is oriented to enable its reading by the RFID scanning systems by ensuring that the tag 110 is separated from any nearby tag and any material that might shield the tag from the radio frequency electrical fields of the RFID scanning systems.

The lower region 182 of the substrate is also provided with an adhesive to allow it to be affixed to the medical item 220.

Figure 2B:
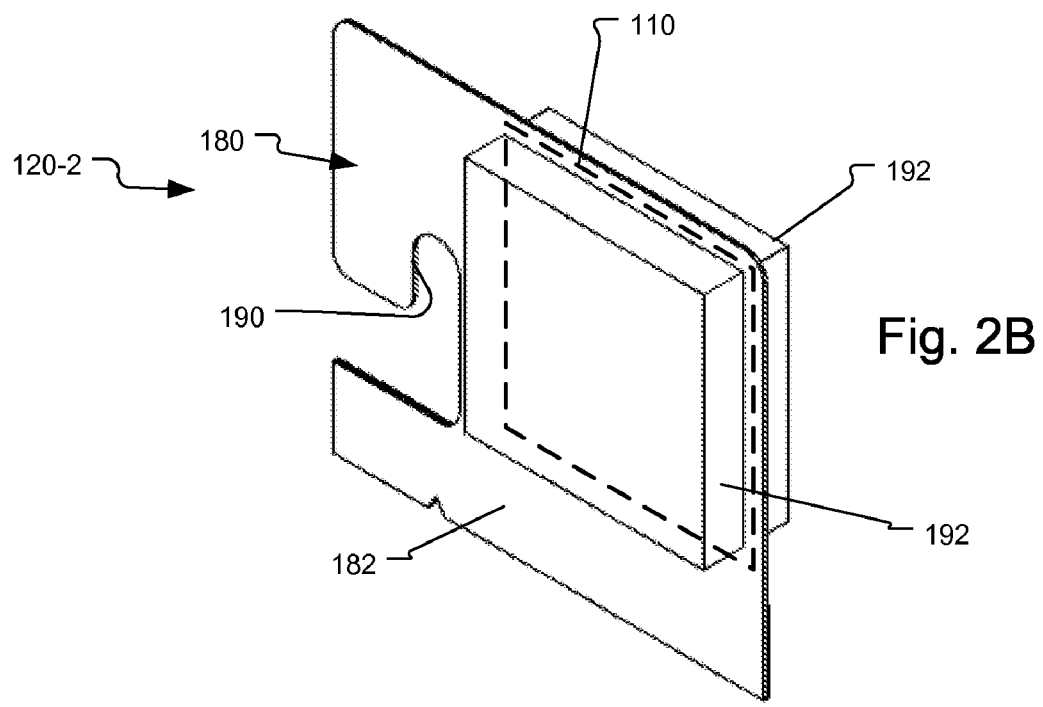

FIG. 2B shows a second embodiment of the tagging device 120-2. In this embodiment, a more rigid RFID tag substrate 180 is provided with a cutout region 190 in the substrate providing a hook. This hook-shaped cutout 190 allows the RFID tag substrate 180 to function to support the medical item on the fixture 152R, 154R of the cabinet 150. In this embodiment, separate spreader members 192 are attached to either side of the substrate 180. The RFID tag 110, in one example is made part of the substrate or adhered to the substrate under one or more of the spreader members 192 Further, in this embodiment the lower portion 182 is also covered with an adhesive for its attachment to the medical item 220 as its hook 222. In this way, this embodiment enables a medical item to be hung on the fixtures 152R, 154R even when the medical item does not otherwise have hook for hanging.

Figure 3:
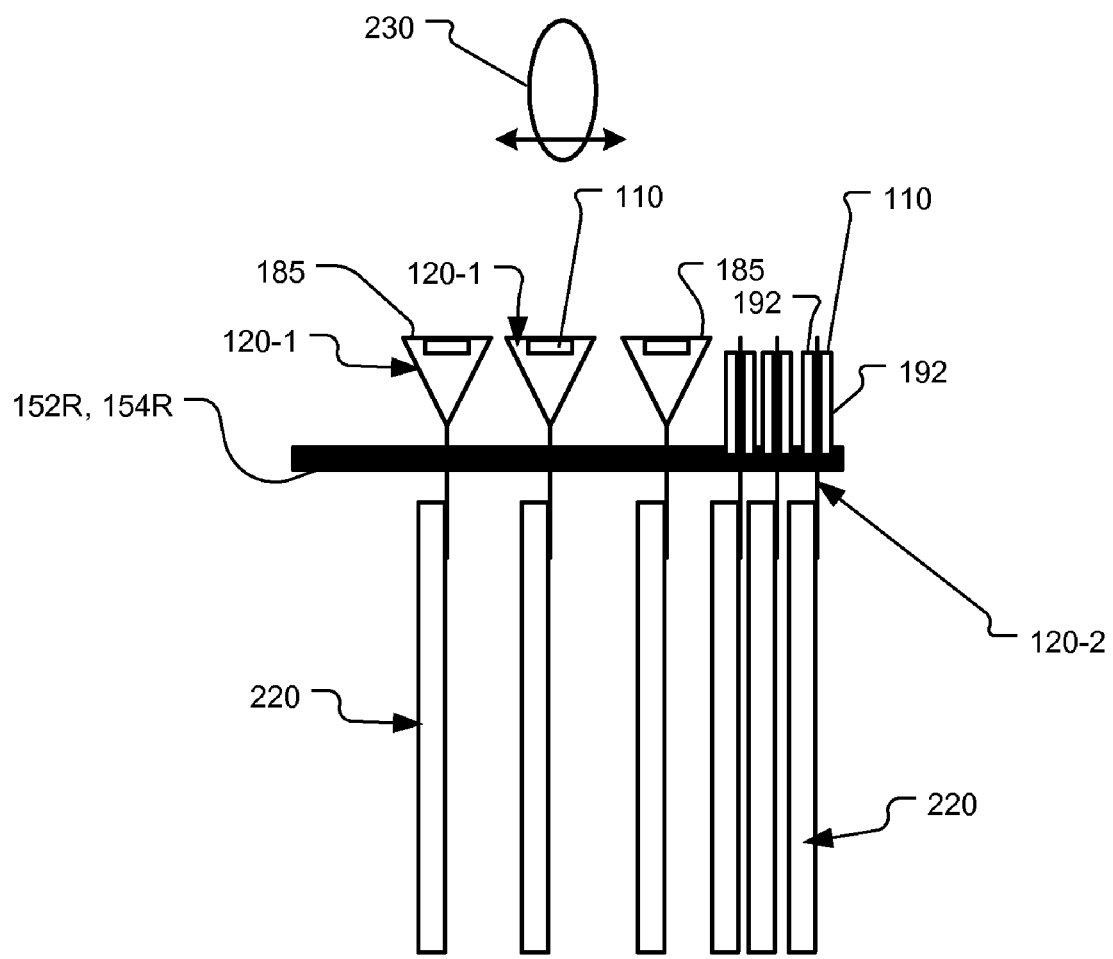
FIG. 3 illustrates the operation of the spreaders for separating the RFID tags of the medical items, according to the present invention.

Fig. 3 shows how the spreaders (185, 192) of the tagging devices 120-1, 120-2 serve to separate the RFID tags 110 to enable their reading by the antenna 230 of the RFID reader. As illustrated, with the separated medical items 220 hanging from the fixture 152R, 154R, the spreaders (185, 192) of the first embodiment tagging system and the second embodiment tagging system function to separate the medical items 220 and specifically their respective RFID tags 110 from each other. This allows the antenna 230, located above the fixture 152R, 154R, to read each of the RFID tags 110 without any other operator intervention. This reading can take place regardless of how the medical items are supported on the fixture 152R, 154R since the spreaders (185, 192) function to keep the medical items/RFID tags sufficiently separated to enable their being read by the antenna/reader.

While this invention has been particularly shown and described with references to preferred embodiments thereof, it will be understood by those skilled in the art that various changes in form and details may be made therein without departing from the scope of the invention encompassed by the appended claims.

What is claimed is:

1. A medical item hanging storage system for medical items comprising:
    storage devices comprising fixtures for holding medical items in a hanging arrangement, and readers for reading radio frequency identification (RFID) tags associated with each of the medical items, the readers including antennas located above the fixtures in the storage devices; and
    tagging devices, being attached to the hanging medical items, including tag substrates and RFID tags that are read by the readers, said RFID tags being attached to the tag substrates; and
    spreaders associated with the tag substrates for separating RFID tags of adjacent medical items and/or other tags to facilitate reading of the RFID tags by the readers;
    wherein the tag substrates comprising hooks and engage the fixtures via the hooks, with the hanging medical items being supported on the fixtures via the tag substrates with the RFID tags being positioned above the fixtures.

2. A system as claimed in claim 1, wherein the readers are integrated into shelves in the storage devices.

3. A system as claimed in claim 1, wherein the tag substrates comprise hooks for engaging the fixtures.

4. A system as claimed in claim 1, wherein the spreaders are attached to the tag substrates.

5. A system as claimed in claim 1, wherein the spreaders are formed by folding the tag substrates.

6. A method for storing and tracking medical items, the method comprising:
    providing fixtures for holding medical items in a hanging arrangement;
    providing hangers including RFID tags for hanging the medical items from said fixtures, said hangers supported by the fixtures with the hanging medical items being supported on the fixtures via the respective hangers, the RFID tags being positioned on the hangers to be above the fixtures;

reading said RFID tags associated with each of the medical items using antennas located above the fixtures; and providing spreaders for separating said RFID tags of adjacent medical items and/or other tags to facilitate reading of the RFID tags.

7. A method as claimed in claim 6, wherein the tag substrates comprise hooks for engaging the fixtures.

8. A medical item hanging storage system for medical items comprising:

storage devices comprising fixtures for holding medical items in a hanging arrangement, and readers for reading tags associated with each of the medical items, the readers comprising antennas located above the fixtures in the storage devices;

tagging devices, being attached to the hanging medical items, including tag substrates and radio frequency identification (RFID) tags that are read by the readers using the antennas, said tags being attached to the tag substrates, and spreaders associated with the substrates for separating stand-off readable RFID tags of adjacent medical items and/or other tags to facilitate reading of the RFID tags by the readers, wherein the tag substrates comprise hooks for engaging the fixtures, with the hanging medical items being supported on the fixtures via the tag substrates, the RFID tags being positioned on the tag substrates to be above the fixtures and the fixtures being positioned above the medical items in the storage system.

9. A system as claimed in claim 1, further comprising a network interface for the storage devices that enables communication with an inventory management system that maintains an inventory database that stores the locations of the medical items by reference to the reading of the RFID tags by the readers.

* * * * *